(12) United States Patent
Ginn

(10) Patent No.: US 12,290,256 B1
(45) Date of Patent: May 6, 2025

(54) SUTURE CUTTER DEVICE AND METHOD OF USE

(71) Applicant: Lonnie J. Ginn, Colleyville, TX (US)

(72) Inventor: Lonnie J. Ginn, Colleyville, TX (US)

( * ) Notice: Subject to any disclaimer, the term of this patent is extended or adjusted under 35 U.S.C. 154(b) by 318 days.

(21) Appl. No.: 17/831,243

(22) Filed: Jun. 2, 2022

(51) Int. Cl.
*A61B 17/04* (2006.01)

(52) U.S. Cl.
CPC ................... *A61B 17/0467* (2013.01)

(58) Field of Classification Search
CPC ............... A61B 17/0467; A61B 17/30; A61B 2017/301; A61B 2017/303; A61B 2017/305
See application file for complete search history.

(56) References Cited

U.S. PATENT DOCUMENTS

| | | | | |
|---|---|---|---|---|
| 5,015,252 A | * | 5/1991 | Jones | A61B 17/30 606/205 |
| 5,122,152 A | * | 6/1992 | Mull | A61B 17/06161 30/294 |
| 5,411,512 A | * | 5/1995 | Abidin | A61B 17/3213 30/151 |
| 9,039,731 B2 | | 5/2015 | Joseph | |
| D788,302 S | | 5/2017 | O'Neill et al. | |
| 2013/0018372 A1 | | 1/2013 | Sims et al. | |

FOREIGN PATENT DOCUMENTS

EP 2659843 B1 7/2015

* cited by examiner

*Primary Examiner* — Katherine H Schwiker
(74) *Attorney, Agent, or Firm* — Richard Eldredge; Leavitt Eldredge Law Firm

(57) ABSTRACT

A suture cutter device for alleviating the number of instrument exchanges during a closing routine of a surgical procedure is disclosed. The suture cutter device comprises of a top segment and a bottom segment. The top segment includes front and rear panels, a plurality of knife blade supports, and a plurality of attachment pin holes. The bottom segment includes a plurality of alignment pins. During use, a knife blade is secured between the plurality of knife blade supports, and the fixed hinge of a tissue forceps is securely coupled to the top segment via a fastening mechanism.

3 Claims, 10 Drawing Sheets

SUTURE CUTTER DEVICE AND METHOD OF USE

BACKGROUND

1. Field of the Invention

The present invention relates generally to suturing instruments, and more specifically to a suture cutter device that securely couples to the base of a grasping type forceps for suture cutting.

2. Description of Related Art

In surgical procedures, the closing or reapproximating of tissue is frequently closed by sutures. Sutures are threadlike materials with mounted needles on one end. Common materials used in sutures include monofilament and multifilament braided strands. Suturing instruments have been developed to assist in closing tissue. Typically, a needle driver, a tissue forceps, and a pair of scissors are used for the sewing, tying and cutting of the suture. After a suture is tied, there are two common lengths to cut the suture above the knot. The length above the knot is often referred to as the suture "tail". Multifilament sutures are often cut with a short "tail" whereas monofilament sutures are cut with a longer "tail" to prevent the knot from unraveling under tension.

Although effective, conventional suturing instruments have limitations. For example, during closing routines of surgical procedures, the surgical team undergoes a counting process of all items used during the procedure including instruments, needles, sponges, and the like. Each count type is documented and numbered in the surgical record (e.g., "First Needle Count", "First Instrument Count", "Second Needle Count", "First Sponge", etc.), and each count often takes several minutes. Generally, the surgeon frequently requests the passing of suturing instruments while closing tissue, resulting in numerous interruptions to these closing counts during the closing routine. These frequent requests place a heavy burden on the surgical team's designated counters, often the instrument nurse, as the counters must perform counts accurately to ensure patient safety. Moreover, multiple counts of each item occur during each layer of closure, making it more tedious and burdensome of passing closing instruments while performing the closing counts.

Accordingly, it is an object of the present invention to provide a suture cutter device that can minimize the exchange of suturing instruments during the sewing portion and counting routines of surgical procedures, thereby reducing the number of counting distractions or interruptions during closing routines.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1A:
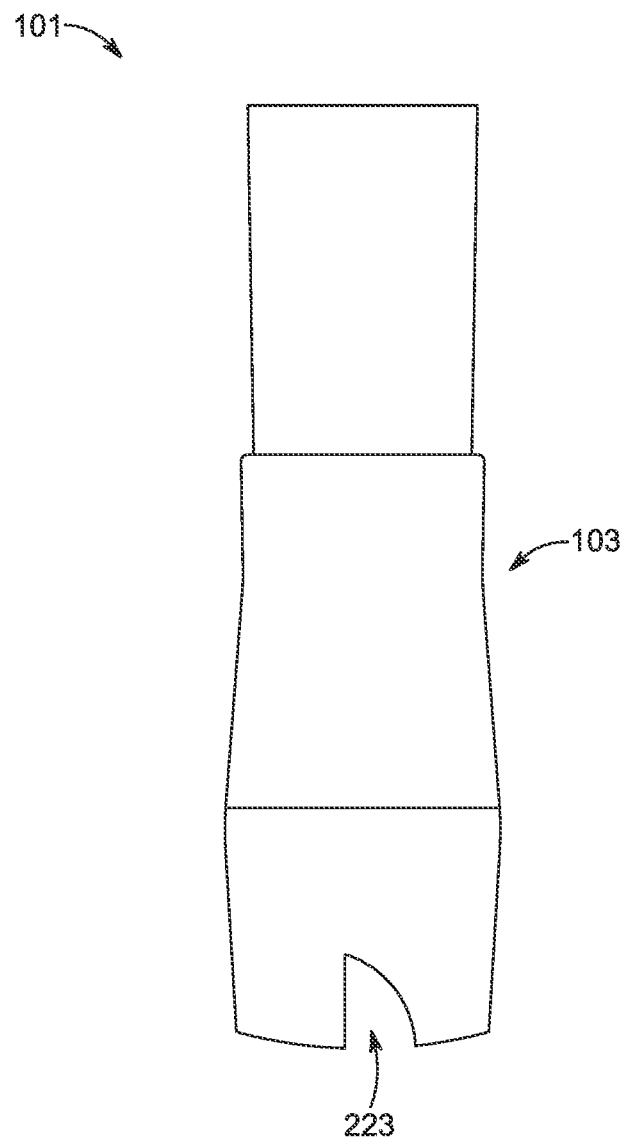
FIG. 1A is a front view of a suture cutter device in accordance with a preferred embodiment of the present invention.
Figure 1B:
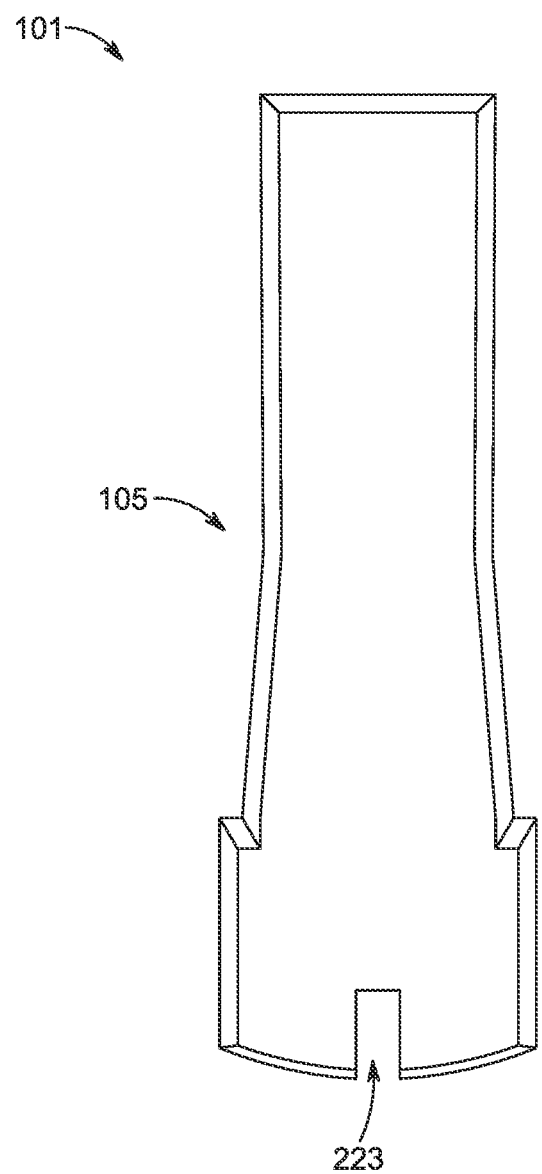
FIG. 1B is a rear view of the suture cutter device of FIG. 1A.
Figure 2A:
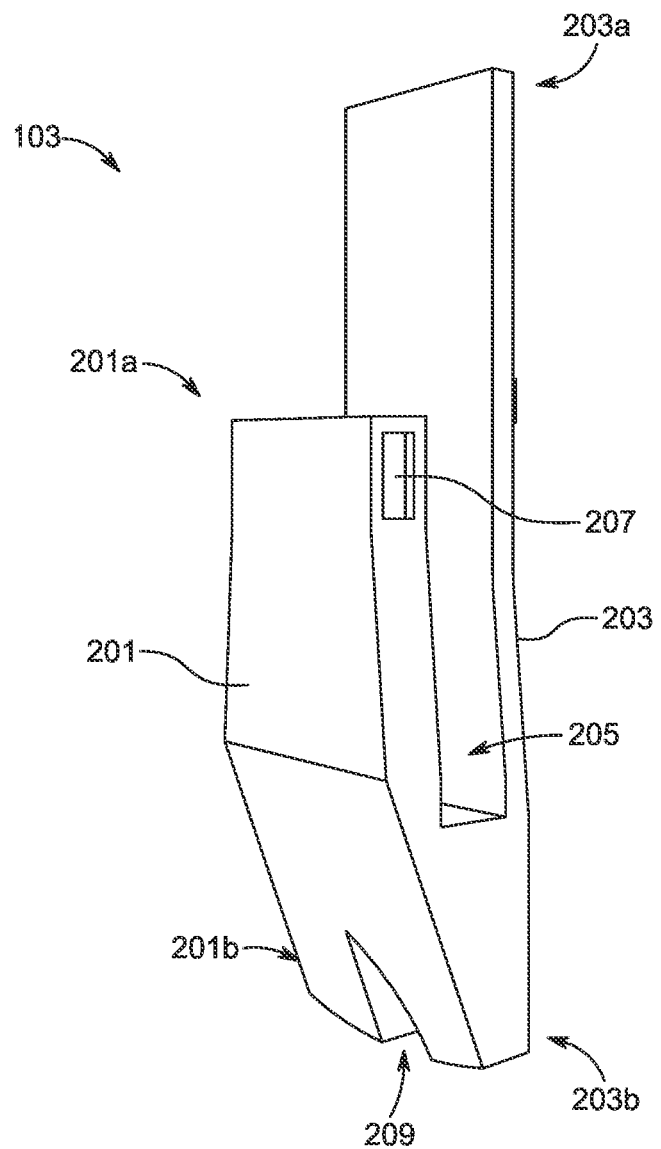
FIG. 2A is a front perspective view of the top segment of FIG. 1A.
Figure 2B:
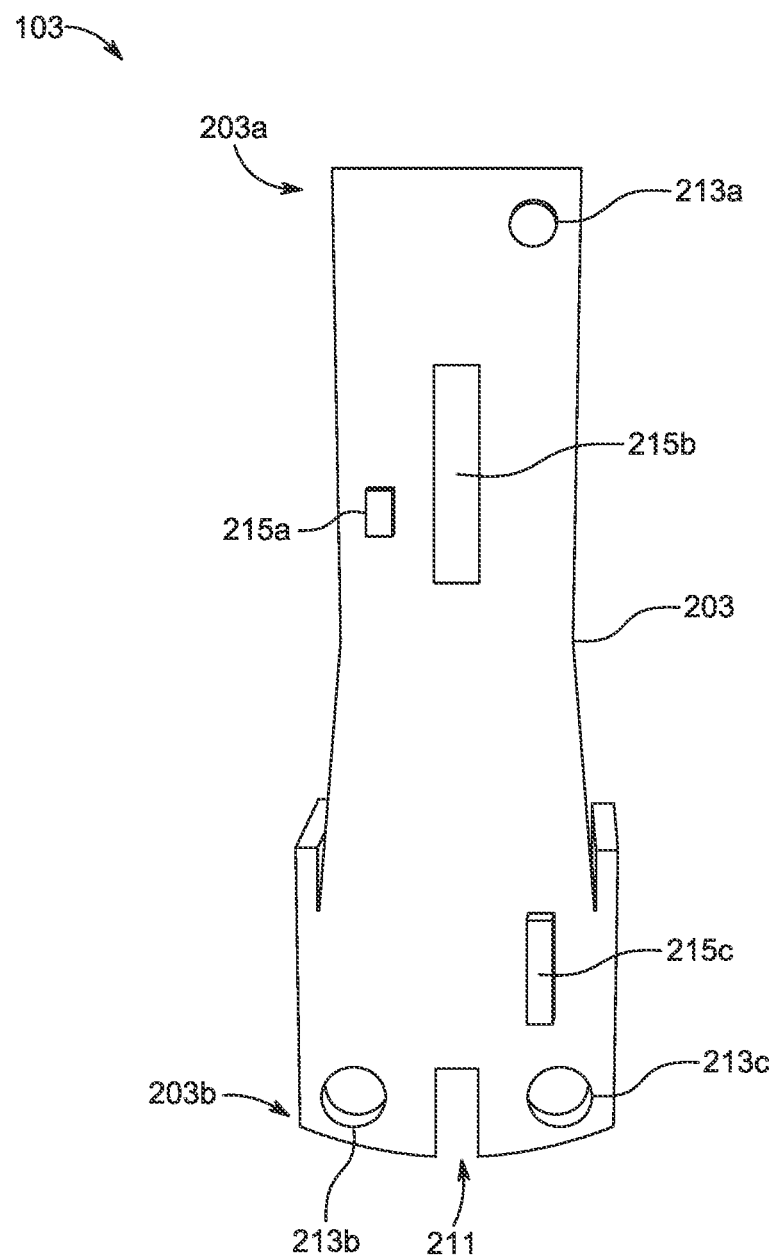
FIG. 2B is a rear view of the top segment of FIG. 2A.
Figure 2C:
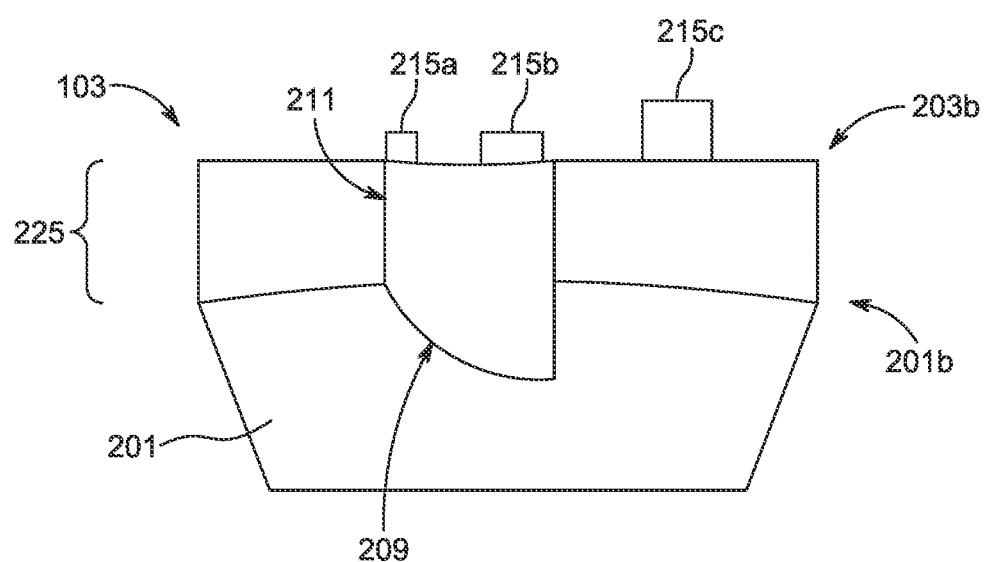
FIG. 2C is a bottom perspective view of the top segment of FIG. 2A.
Figure 2D:
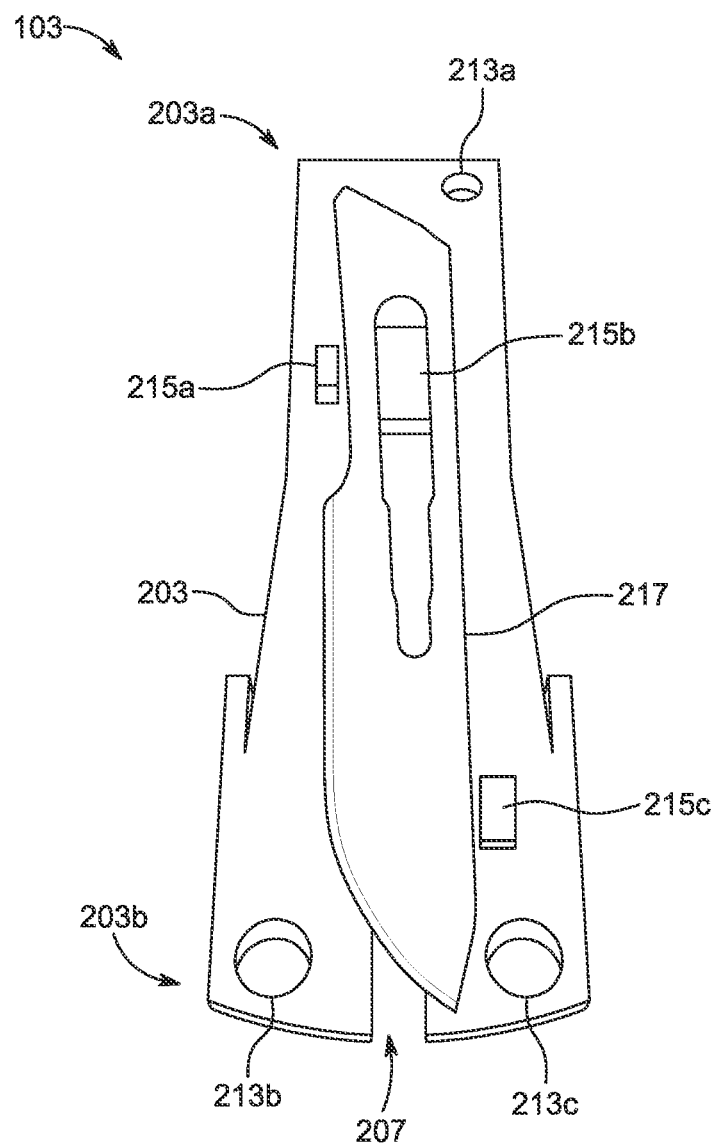
FIG. 2D is a rear perspective view of the top segment of FIG. 2A, illustrating a knife blade inserted therein.
Figure 3A:
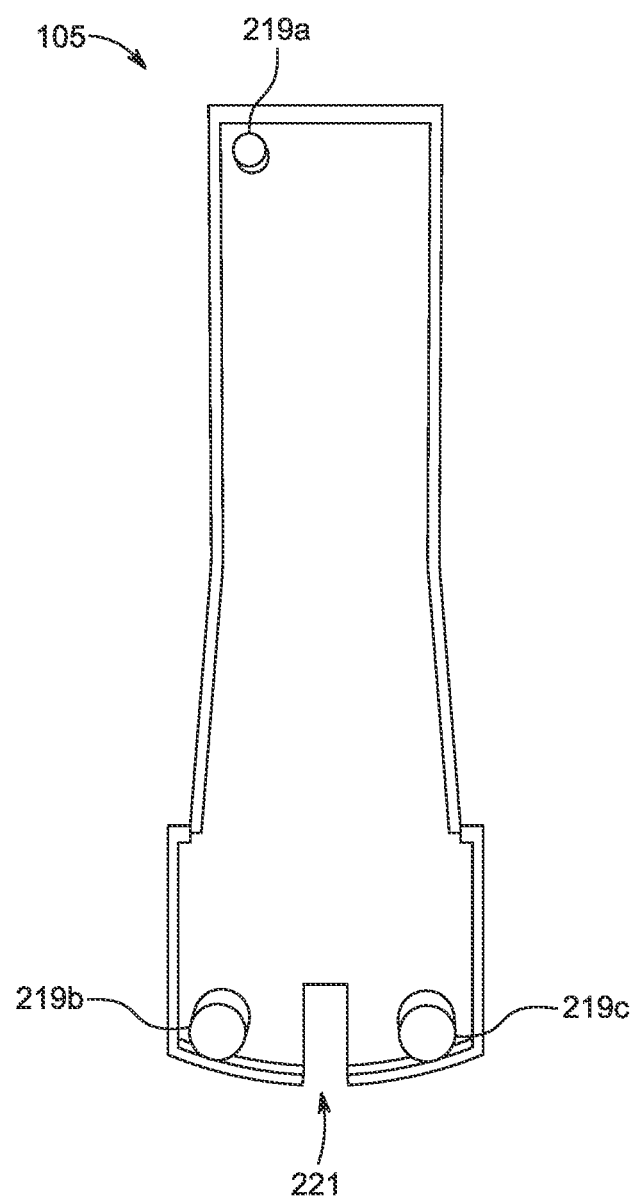
FIG. 3A is a front view of the bottom segment of FIG. 1A.
Figure 3B:
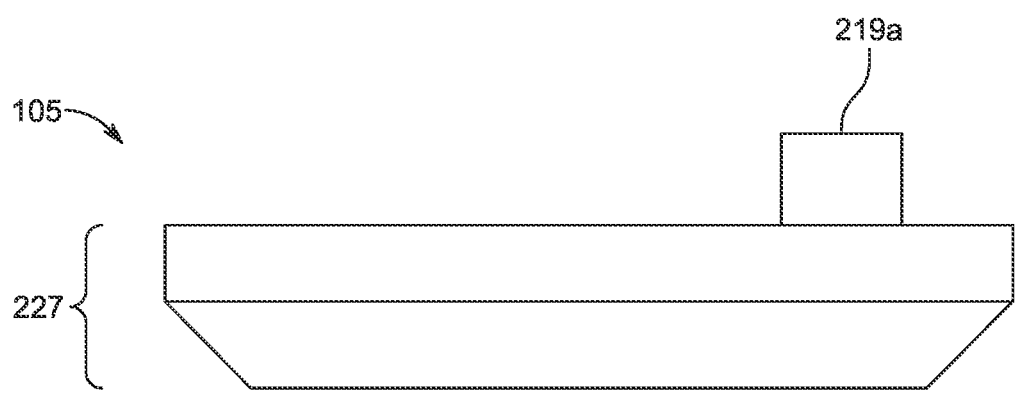
FIG. 3B is a bottom perspective view of the bottom segment of FIG. 3A.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional suturing instruments. Specifically, the present invention provides a means for attaching a blade to a tissue grasping forceps for suture cutting, thereby improving suturing efficiency. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIGS. 1A through 3B depict various views of a suture cutter device 101 in accordance with a preferred embodiment of the present application. It will be appreciated that the suture cutter device 101 overcomes one or more of the above-listed problems commonly associated with conventional suturing instruments.

In the contemplated embodiment, the suture cutter device 101 includes a top segment 103 and a bottom segment 105. The top segment 103 comprises of a front panel 201 having a first end 201a and a second end 201b, and a rear panel 203 having a first end 203a and a second end 203b. The front panel 201 couples to the rear panel 203 via the second ends 201b, 203b, creating a cavity 205 therebetween for the mounting of a fixed hinge of a tissue forceps (not shown, see FIG. 4). The first end 201a includes a channel 207 configured to allow a fastening mechanism (not shown, see FIG. 4) to pass therethrough.

The second end 201b includes an opening 209 configured in the shape of a knife blade. The second end 203b includes an opening 211 configured in a generally rectangular shape. It should be appreciated that the opening 211 can have any other suitable configuration.

The rear panel 203 includes a plurality of attachment pin holes (e.g., first pin hole 213a, second pin hole 213b, third pin hole 213c), generally referred to as attachment pin holes 213. The rear panel 203 further includes a plurality of knife blade supports (e.g., first knife blade support 215a, second knife blade support 215b, third knife blade support 215c), generally referred to as knife blade supports 215. The knife blade supports 215 are configured to stabilize a knife blade 217 when inserted against the rear panel 203.

The bottom segment 105 includes a plurality of alignment pins (e.g., first alignment pin 219a, second alignment pin 219b, third alignment pin 219c), generally referred to as alignment pins 219, which insert into the attachment pin holes 213, thereby coupling the bottom segment 105 to the top segment 103. It should be appreciated that the location of the attachment pin holes 213 and the alignment pins 219 can vary.

The bottom segment 105 also includes an opening 221 configured in a generally rectangular shape. It should be appreciated that the opening 221 can have any other suitable configuration.

It should also be appreciated that openings 209, 211, 221 create a cutting slot 223 for the user to access a knife blade that is mounted within the cavity 207 for suture cutting.

The suture cutter device 101 further includes a first cutting depth gauge 225 located proximate a bottom portion of the top segment 103 and a second cutting depth gauge 227 located proximate a bottom portion of the bottom segment 105. The first cutting depth gauge 225 provides for long suture tail lengths. The second cutting depth gauge 227 provides for short suture tail lengths. It should be appreciated that the cutting depth gauges 225, 227 are configured to accommodate a desired suture tail length, thereby enhancing the versatility of the suture cutter device 101 for various suture types including monofilament and multifilament sutures.

Additionally, it should be appreciated that the suture cutter device 101 may be made from any suitable or desired materials, including conventional materials known and used in the art.

Figure 4:
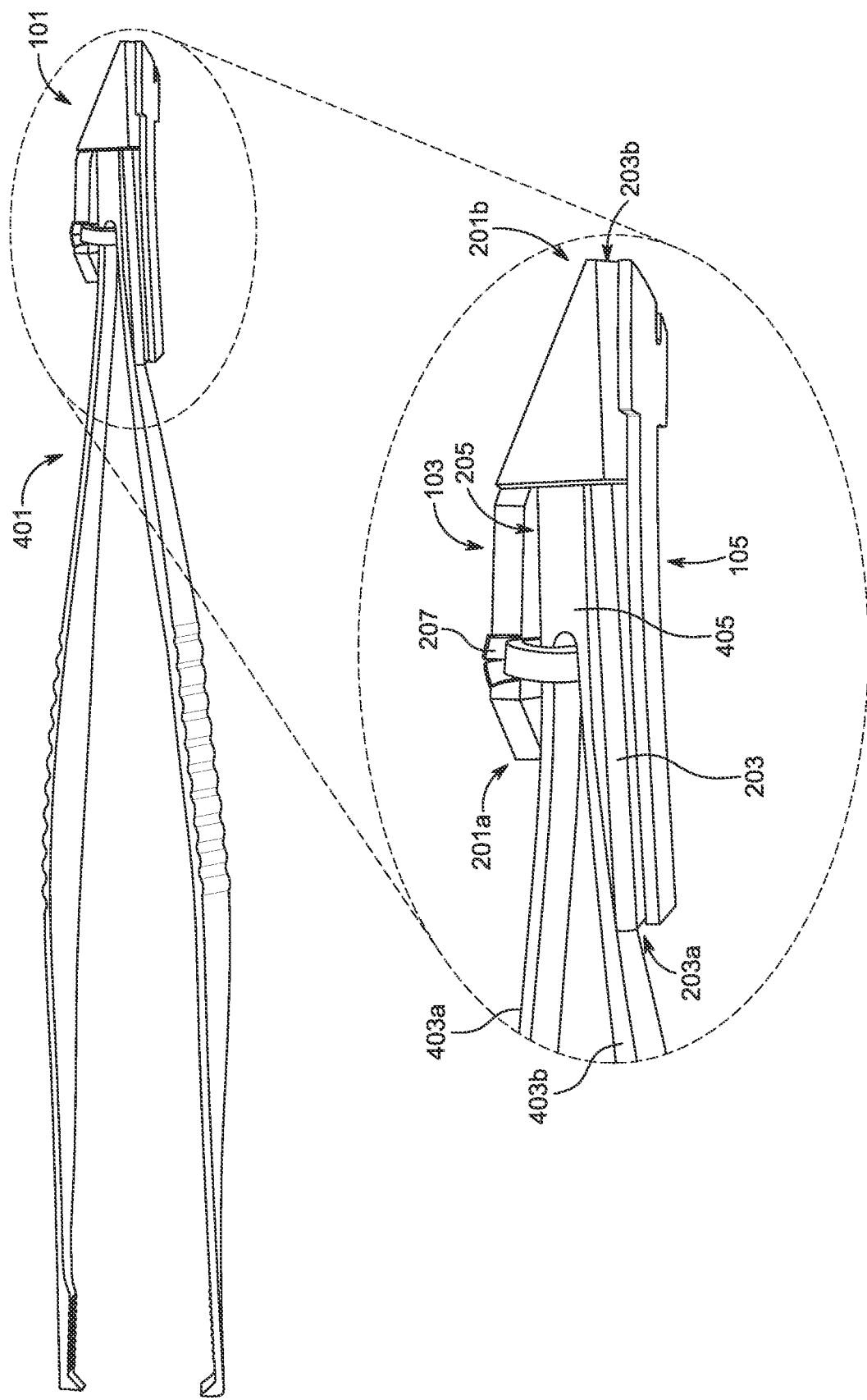
FIG. 4 is a profile view of the suture cutter device of FIG. 1A attached to a tissue forceps.

In FIG. 4, a profile view of the suture cutter device 101 attached to a tissue forceps 401 is illustrated. As shown, the tissue forceps 401 includes a pair of shanks 403a, 403b coupled via a fixed hinge 405. During use, the fixed hinge 405 is inserted into the cavity 205 and secured to the suture cutter device via a fastening mechanism 407. In the preferred embodiment, the fastening mechanism 407 is a zip tie-type of fastener.

It should be appreciated that the suture cutter device 101 can be integrally formed as part of the fixed hinge of a tissue forceps. In addition, it should be appreciated that the suture cutter device 101 can be manufactured as a disposable single-use attachment.

It should also be appreciated that one of the unique features believed characteristic of the present application is the secure and safe attachment of a knife blade to a tissue forceps for reducing the number of instrument exchanges during closing of tissue. In addition, the present application is considered unique because of its inclusion of cutting depth gauges 225, 227 which accommodates both short and long suture tail lengths.

Figure 5:
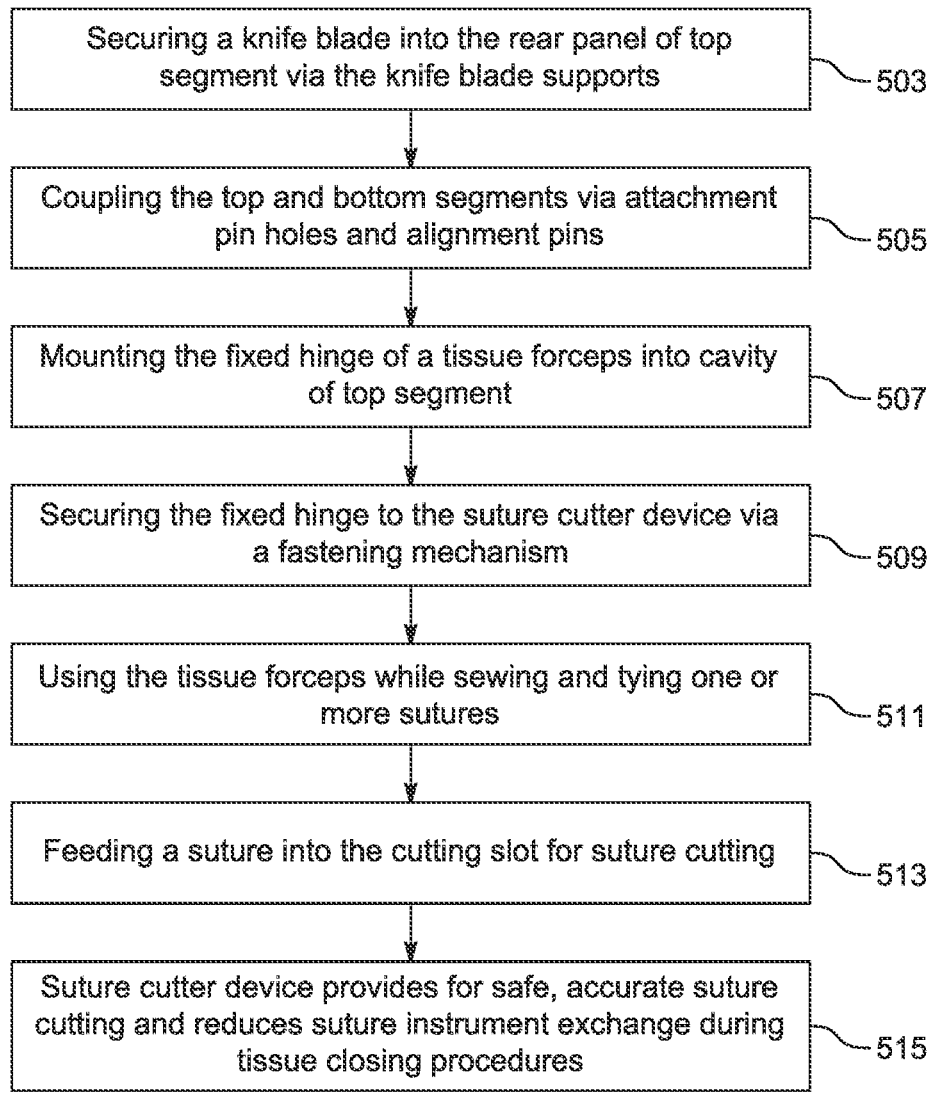
FIG. 5 is a flowchart of a method of use of the suture cutter device of FIG. 1A.

In FIG. 5, a flowchart 501 depicts a simplified method of use associated with the suture cutter device 101. During use, a knife blade is secured into the top segment's rear panel via the knife blade supports, as shown with box 503. Then, the top and bottom segments are coupled via attachment pin holes and alignment pins, as shown with box 505. Next, the fixed hinge of a tissue forceps is mounted within the top segment's cavity and secured via a fastening mechanism, as shown with boxes 507, 509. The user can then utilize the tissue forceps for sewing and tying one or more sutures and can feed a suture into the cutting slot for suture cutting, as shown with boxes 511, 513. The suture cutter device provides for safe, accurate suture cutting and reduces suture instrument exchange during tissue closing procedures, as shown with box 515.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A suture cutter device, comprising:
    a top segment, the top segment having:
        a front panel, the front panel having:
            a first end; and
            a second end having channel for allowing a fastening mechanism to pass therethrough, and a first opening;
        a rear panel, the rear panel having:
            first end;
            a second end;
            a plurality of blade supports configured to stabilize a knife blade therebetween
            a plurality of attachment pin holes; and
            a second opening having a rectangular shape;

wherein the front and rear panels engage via the second ends; and a bottom segment, the bottom segment having:
  a plurality of alignment pins; and
  a third opening having a rectangular shape;
wherein the top and bottom segments securely couple via the insertion of the plurality of alignment pins into the plurality of attachment pin holes; and
wherein the first, second, and third openings create a cutting slot for a suture to feed therethrough for suture cutting.

2. The suture cutter device of claim 1, further comprising:

a first cutting depth gauge located proximate a bottom portion of the top segment, the first cutting depth gauge configured to accommodate a desired suture tail length; and a second cutting depth gauge located proximate a bottom portion of the bottom segment the second cutting depth gauge configured to accommodate a desired suture tail length.

3. A method for alleviating the number of instrument exchanges during a closing routine of a surgical procedure, the method comprising:

providing the suture cutter device of claim 1;

securing h knife blade into the rear panel of the top segment via the plurality of knife blade supports;

coupling the top and bottom segments via the coupling of the plurality of attachment pin holes and the plurality of alignment pins;

mounting a fixed hinge of a tissue forceps within the cavity of the top segment;

securing the fixed hinge to the suture cutter device via a fastening mechanism;

using the tissue forceps while sewing and tying one or more sutures; and feeding a suture into the cutting slot for suture cutting.

* * * * *